US009285376B2

(12) United States Patent
Spinke et al.

(10) Patent No.: US 9,285,376 B2
(45) Date of Patent: Mar. 15, 2016

(54) MEASURING RANGE EXTENSION OF CHROMATOGRAPHIC RAPID TESTS

(71) Applicant: Roche Diagnostics Operations, Inc., Indianapolis, IN (US)

(72) Inventors: Jürgen Spinke, Lorsch (DE); Marcel Thiele, Mannheim (DE); Jürgen Schäffler, Weinheim (DE); Andreas Nufer, Bad Dürkheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/330,179

(22) Filed: Jul. 14, 2014

(65) Prior Publication Data

US 2014/0322703 A1    Oct. 30, 2014

Related U.S. Application Data

(63) Continuation of application No. 11/853,100, filed on Sep. 11, 2007, now abandoned.

(30) Foreign Application Priority Data

Sep. 11, 2006  (EP) ................................. 06019008

(51) Int. Cl.
  *G01N 33/543*  (2006.01)
  *G01N 33/74*  (2006.01)
  *G01N 33/53*  (2006.01)
  *G01N 33/557*  (2006.01)

(52) U.S. Cl.
  CPC ............ *G01N 33/74* (2013.01); *G01N 33/5306* (2013.01); *G01N 33/54386* (2013.01); *G01N 33/557* (2013.01)

(58) Field of Classification Search
  None
  See application file for complete search history.

(56) References Cited

U.S. PATENT DOCUMENTS

| 2003/0100128 A1 | 5/2003 | Kenjyou et al. |
| 2003/0224534 A1 | 12/2003 | Kawate |
| 2004/0029177 A1 | 2/2004 | Nadaoka et al. |
| 2004/0096985 A1 | 5/2004 | Kenjyou et al. |
| 2004/0241047 A1 | 12/2004 | Buechler et al. |
| 2005/0107956 A1 | 5/2005 | Fukunaga et al. |
| 2005/0250141 A1 | 11/2005 | Lambert et al. |
| 2006/0089810 A1 | 4/2006 | Matsumoto et al. |
| 2007/0059767 A1 | 3/2007 | Karl et al. |
| 2007/0259450 A1 | 11/2007 | Bodenbach et al. |
| 2008/0206782 A1 | 8/2008 | Golden et al. |

FOREIGN PATENT DOCUMENTS

| CA | 2359667 | 8/2000 |
| EP | 0648288 | 4/1995 |
| JP | 05010953 | 1/1993 |
| JP | 06096697 | 4/1994 |
| JP | 08075740 | 3/1996 |
| WO | WO9624062 | 8/1996 |
| WO | WO0045176 | 8/2000 |
| WO | WO2004059293 | 7/2004 |

OTHER PUBLICATIONS

Struthers, et al., "How to use natriuretic peptide levels for diagnosis and prognosis", European Heart Journal (1999) 20,1474-1375.

Hunt, et al., "Immunoreactive amino-terminal pro-brain natriuretic peptide (NT-PROBNP): a new marker of cardiac impairment", Clin. Endocrinol. 47 (1997) 287-296.

Talwar, et al., "Plasma N-terminal pro-brain natriuretic peptide and the ECG in the assessment of left-ventricular systolic dyusfunction in a high risk population", European Heart Journal 91999) 20, 1736-1744.

OTHER PUBLICATIONS

Lagerstedt et al, "Measurement of Plasma Free metanephrine and Normetanephrine by Liquid Chromoatography-Tandem Mass Spectrometry for Diagnosis of Phenochromocytoma", Clinical Chemistry 50:3 (2004) 603-611.

Shin, et al., "An Improved, Reliable and Practical Kinetic Assay for the Detection of Prekalikrein Activator in Blood Products", Arch Pharm Res, vol. 24, No. 4, (2002) 505-510.

*Primary Examiner* — Gary W Counts
(74) *Attorney, Agent, or Firm* — McDonnell Boehnen Hulbert & Berghoff LLP

(57) ABSTRACT

A method for the quantitative determination of an analyte in a sample is provided comprising: (a) providing an analyte-specific substance which is able to undergo a reaction which generates a detectable signal when it is contacted with an analyte; (b) providing at least two calibration graphs which have been generated by reacting in each case the same analyte-specific substance with different amounts of in each case the same test analyte for in each case a predetermined reaction time; (c) contacting the analyte-specific substance with a sample which contains the analyte to be detected; (d) measuring the signal at a first predetermined reaction time for which a first calibration graph according to (b) is provided; (e) checking whether the signal measured according to (d) enables a quantitative determination of the analyte with a desired accuracy; (f) (i) quantitatively determining the analyte on the basis of the signal measured according to (d) if the desired accuracy is reached, or (ii) measuring the signal at a second predetermined reaction time for which a second calibration graph according to (b) is provided; (g) checking whether the signal measured according to (f(ii)) enables a quantitative determination of the analyte with a desired accuracy; and (h) (i) quantitatively determining the analyte on the basis of the signal measured according to f(ii) if the desired accuracy is reached, or (ii) continuing the determination at at least one further predetermined reaction time (corresponding to (f)(ii), (g), (h)(i)).

24 Claims, 2 Drawing Sheets

US 9,285,376 B2

MEASURING RANGE EXTENSION OF CHROMATOGRAPHIC RAPID TESTS

RELATED APPLICATION

This application is a continuation of U.S. patent application Ser. No. 11/853,100, filed Sep. 11, 2007, now abandoned, which claims priority to European Patent Application Serial No. 06 019 008.9, filed Sep. 11, 2006.

BACKGROUND OF THE INVENTION

The present invention relates generally to methods and devices for the quantitative determination of an analyte in a sample and, in particular, to methods for extending the quantitative measuring range of an analyte in a sample, and test devices employing same.

A widespread analytical method for the rapid determination of analytes such as, for example, drugs, pregnancy hormones, infectious diseases or cardiac markers utilizes immunological test strips. In this connection qualitative tests that are read purely visually (e.g., Roche CARDIAC® D-dimer, Trop T sensitive, etc.) as well as quantitative tests that are evaluated by means of a reading device (e.g., Elecsys® proBNP, Roche CARDIAC® proBNP, etc.) are widely used. Such quantitative immunological test strips are characterized in particular by their easy handling. The test strips are usually based on the fact that the test strip contains a reagent which leads to a detectable signal by reaction with the analyte in the sample. The detectable signal is usually determined by reflectance measurement after a specified time period. The time period between contacting the analyte and reagent and measuring the signal is chosen to be as long as possible. This ensures a long reaction time between the reagent and analyte and thus ensures the highest possible sensitivity of such test strips. However, for reasons of reaction kinetics it is no longer possible after such a long reaction period to quantitatively determine analytes which are present in a high concentration in a sample.

Hence, such test strips still have considerable weaknesses with regard to their performance compared to conventional laboratory analytical systems such as, e.g., Elecsys® (Roche Diagnostics), IM (Abbott), Dimension® (Dade Behring). Especially the measuring accuracy and the dynamic measuring range are considerably impaired in test strips for example in comparison to reactions involution. This limits their use when determining analytes which require a high sensitivity as well as the measuring range as large as possible. In particular, for the emergency care of patients it would be very helpful for the attending physician if a test or a method could be provided which, due to its high sensitivity, could, on the one hand, enable certain diseases to be reliably excluded but, on the other hand, would also provide a large measuring range. A large measuring range for an analyte is particularly desirable for risk stratification and for therapeutic monitoring. A measuring range extension of tests would be particularly desirable for those pathological conditions in which the concentration of an analyte or marker that is characteristic for the condition correlates with the severity of the pathological condition. An elevated marker concentration (e.g., NT-proBNP) can in such cases indicate an increased risk situation for a patient.

SUMMARY OF THE INVENTION

It is against the above background that the present invention provides certain unobvious advantages and advancements over the prior art. In particular, the inventors have recognized a need for improvements in methods for extending the quantitative measuring range of an analyte in a sample.

Although the present invention is not limited to specific advantages or functionality, it is noted that the methods according to the invention enable the upper limit of the measuring range to be increased by more than three-fold compared to the known methods of the prior art. The methods according to the invention thus improve the diagnostic competence of the attending physician.

The extended measuring range of a test according to the invention may also enable additional, often laborious tests (e.g., invasive diagnostic methods, etc.) to be dispensed with.

As described in detail below, the methods according to the invention enable a more rapid determination of concentrations than methods or tests that have been described in the prior art especially with high analyte concentrations in a sample. Since, for example, the blood levels of NT-proBNP correlate with the degree of cardiac dysfunction, the methods according to the invention allow a more rapid assessment of the cardiospecific status of a patient in emergency situations. This gives rise to the advantage that when acute cardiac events occur such as for example an acute myocardial infarction, patients can be identified and adequately treated at an earlier time than is the case with the current diagnostic procedures. The methods according to the invention and the ability to make a more rapid diagnosis especially in the case of an acute cardiac event, enable the attending physician to more rapidly initiate appropriate countermeasures and can thus reduce other cardiac complications and the mortality rate.

In accordance with one embodiment of the present invention, a method for the quantitative determination of an analyte in a sample is provided comprising:
(a) providing an analyte-specific substance which is able to undergo a reaction which generates a detectable signal when it is contacted with an analyte,
(b) providing at least two calibration graphs which have been generated by reacting in each case the same analyte-specific substance with different amounts of in each case the same test analyte for in each case a predetermined reaction time,
(c) contacting the analyte-specific substance with a sample which contains the analyte to be detected,
(d) measuring the signal at a first predetermined reaction time for which a first calibration graph according to (b) is provided,
(e) checking whether the signal measured according to (d) enables a quantitative determination of the analyte with a desired accuracy,
(f) (i) quantitatively determining the analyte on the basis of the signal measured according to (d) if the desired accuracy is reached, or
  (ii) measuring the signal at a second predetermined reaction time for which a second calibration graph according to (b) is provided,
(g) checking whether the signal measured according to (f)(ii) enables a quantitative determination of the analyte with a desired accuracy, and
(h) (i) quantitatively determining the analyte on the basis of the signal measured according to (f)(ii) if the desired accuracy is reached, or
  (ii) continuing the determination at least one further predetermined reaction time (corresponding to (f)(ii), (g), (h)(i)).

The method can further comprise:
(i) measuring the signal at a third predetermined reaction time for which a third calibration graph according to (b) is provided,
(j) checking whether the signal measured according to (i) enables a quantitative determination of the analyte with a desired accuracy, and
(k), (i) quantitatively determining the analyte on the basis of the signal measured according to (i) if the desired accuracy is reached, or
(ii) continuing the determination at least one further predetermined reaction time.

The steps (f)(ii), (g) and (h)(i) of the method can be repeated as often as desired. In a typical embodiment these steps are repeated two or three times; i.e., two or three calibration graphs for two or three predetermined reaction times are generated or provided.

In accordance with yet another embodiment of the present invention, a method for the quantitative determination of an analyte in a sample is provided comprising:
(a) providing an analyte-specific substance which is able to undergo a reaction which generates a detectable signal when it is contacted with an analyte,
(b) providing at least two calibration graphs which have been generated by reacting in each case the same analyte-specific substance with different amounts of in each case the same lest analyte for in each case a predetermined reaction time,
(c) contacting the analyte-specific substance with a sample which contains the analyte to be detected,
(d) measuring a first signal at a first predetermined reaction time for which a first calibration graph according to (b) is provided,
(e) measuring a second signal at a second predetermined reaction time for which a second calibration graph according to (b) is provided,
(f) optionally measuring a further signal,
(g) checking which of the signals measured according to (d), (e) or (f) enables a sufficient accuracy for the quantitative determination of the analyte, and
(h) quantitatively determining the analyte on the basis of the signal which enables an adequate accuracy.

In order to check whether the first measured signal or the second measured signal enables the analyte to be quantitatively determined with a greater accuracy, an empirical concentration limit is defined in a typical embodiment on the basis of the at least two calibration graphs that are provided. Analyte concentrations which exceed this limit are evaluated according to the shorter of the two reaction times whereas analyte concentrations which fall below this limit are determined according to the longer of the two reaction times. If it is found that the analyte concentration exceeds the limit after the short reaction time, i.e., a high analyte concentration is determined, the method can be stopped at this time.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood and is elucidated in more detail when read in conjunction with the following drawings, where like structure is indicated with like reference numerals and in which.

DETAILED DESCRIPTION OF THE INVENTION

Figure 1:
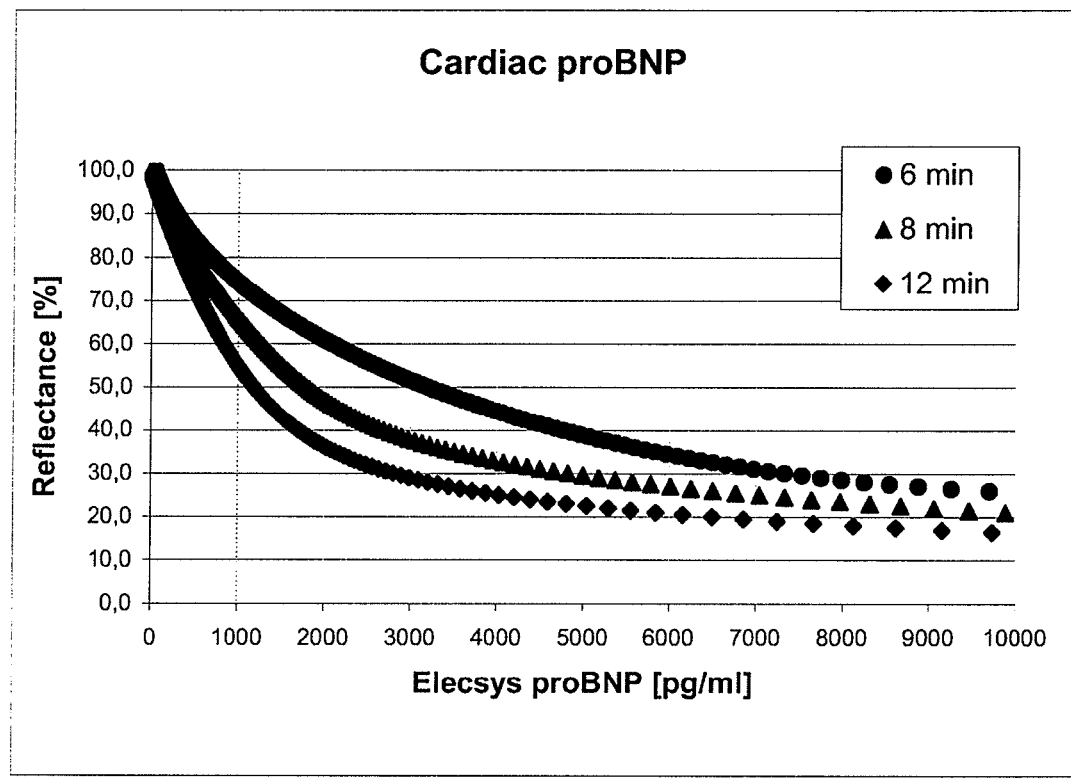
FIG. 1 shows the reflectance kinetics of CARDIAC® proBNP after 6 min, 8 min and 12 min. The reflectance [%] is plotted against the concentration of proBNP [pg/ml] which was determined by the Elecsys® proBNP reference test.

In accordance with a typical embodiment of the present invention, a liquid sample typically derived from body fluid is used. A blood, plasma, serum, saliva or urine sample is more typically used.

The analyte to be determined quantitatively is typically selected from nucleic acids, lipids, carbohydrates, proteins and in particular from DNA, RNA, antibodies, antigens, metabolic products, hormones, viruses, microorganisms, cell, cardio-specific markers, neurohormonal markers, ischaemic markers and muscle-specific markers.

Typical examples of lipids include cholesterol, HDL cholesterol and triglycerides. A typical carbohydrate analyte is glucose. Examples of enzymes to be determined include alkaline phosphatase and amylase. Uric acid, bilirubin and urobilinogen are examples of typical metabolic products.

Examples of neurohormonal markers include atrial (A-type) natriuretic peptide (ANP), B-type natriuretic peptide (BNP) or N-terminal fragments of the respective propeptides NT-ProANP and NT-ProBNP.

Examples of ischaemic markers include ischaemically modified albumin (IMA), fatty acid binding protein, free fatty acid, pregnancy associated plasma-protein A, glycogen phosphorylase isoenzyme BB and sphingosine-1-phosphate.

Myoglobin and creatine kinase MB (CK-MB) are typical examples of muscle-specific markers.

CD40 is a typical example of a marker for platelet-activation.

Typical cardiospecific ischaemic-necrotic markers are troponin T or troponin I.

In another typical embodiment at least one cardiac marker or cardio-specific marker is determined which can in turn be selected from troponin T, myoglobin, D-dimer and NT-proBNP.

The analyte-specific substance is typically selected from receptors, antibodies, antigens, lectin, nucleic acids and nucleic acid analogues that can bind to the analyte. The analyte-specific substance is typically additionally coupled to a detection reagent or to an enzyme which generates a detectable signal when it binds to the analyte. In a typical embodiment, the binding of the analyte to the analyte-specific substance leads, by means of a reaction, directly to a detectable signal. In a further embodiment a substrate can be added after the analyte has bound to the analyte-specific substance, said substrate being converted either by the analyte or by the analyte-specific substance while emitting a detectable signal. Typical detection systems are for example colloidal metal particles, in particular, gold, fluorescent nanoparticles, e.g., latex, up-converting phosphors, quantum dots or superparamagnetic particles.

The detection of the analyte BNP or NT-proBNP which are typically determined according to the invention is for example described in Struthers (Eur. Heart J. 20 (1999), 1374-1375), Hunt et al., Clin. Endocrinol. 47 (1997, 287-

296), Talwar et al. (Eur. Heart J. 20 (1999), 1736-1744), and in EP-0 648 228 and WO 00/45176.

In a typical embodiment of the present invention the reaction between the analyte and analyte-specific substance is an immunological reaction.

A "calibration graph" in the sense of the present invention is understood as a function which is derived by allocating defined amounts of test analyte to defined parameters that describe the detectable signal. In this process a defined amount of test analyte is allocated to a parameter describing a defined signal in this process. Average values which are derived from a plurality of typically independent measurements can also be used to generate calibration graphs.

The parameters describing the detectable signal are typically parameters which describe an absorption or emission of light of any wavelength as a result of the reaction of the analyte with the analyte-specific substance. Typical examples of the parameters describing the signal are reflectance, emission and absorption values. Furthermore, it is also for example possible to use magnetic particles so that magnetic fields (magnetic field states) also come into consideration as parameters describing the signal.

The parameters describing the detectable signal are typically measured by reacting the in each case same analyte specific substance with different amounts of the in each case same analyte for in each case a predetermined reaction time. For this the respective amount of the in each case same test analyte is reacted with the in each case same analyte specific substance and the detectable signal is measured after the predetermined reaction time. This means that in each case the same analyte-specific substance and the in each case same test analyte are used in different amounts to generate a calibration graph. 5 to 50 different amounts of test analyte, i.e., different individual reactions and, more typically, 10 to 40 individual reactions and, most typically, 10 to 25 individual reactions are carried out for a corresponding number of allocations of test analyte amount to signal-describing parameter per predetermined reaction time in order to generate a calibration graph.

Before generating the calibration graphs the experimentally determined values can also be subjected to a kinetic evaluation process in which case the values determined by the evaluation process can be used to generate the calibration graph.

The test analyte and the analyte to be detected quantitatively are typically identical.

In accordance with an embodiment of the invention, the generated calibration graphs are used as a basis for checking whether the measured signal which results from the reaction of the analyte-specific substance with the analyte in the sample is sufficient for a quantitative determination of the analyte with a desired accuracy. The accuracy can be checked using any evaluation procedures known in the special field which take into account signal amplitude or precision.

In a typical embodiment of the present invention the signal measured after a predetermined reaction time between the analyte and analyte-specific substance is compared with the calibration graph provided for the corresponding predetermined reaction time. The desired accuracy for the amount of analyte to be determined is achieved when the observed calibration graph has the greatest slope for the corresponding amount of test analyte out of all predetermined calibration curves.

The at least two predefined reaction times for determining the calibration graphs are selected such that higher concentrations of analyte in the sample can be detected and also the required test sensitivity is achieved. In order to achieve the required test sensitivity it is necessary to have the reaction time as long as possible. With shorter reaction times fewer complexes and typically immune complexes are formed between the analyte-specific substance and analyte. Correspondingly lower signal intensity is detected. In contrast, in the case of low analyte concentrations too few complexes and typically immune complexes are formed and the sensitivity of the test is lost. However, in the case of high concentrations substantially more complexes are available so that even with short reaction times clear signals and high signal intensities can be detected. The quantitative measuring range of the reaction between analyte and analyte-specific substance is considerably increased by combining a long reaction time which ensures the required sensitivity with a short reaction time, which is used to detect higher concentrations.

For this reason a long reaction time with regard to the reaction of analyte and analyte-specific substance is selected as a predetermined reaction time after which the reaction between the analyte and analyte-specific substance is in a saturation range or a stationary state. Further, predetermined reaction/times are typically selected to be correspondingly shorter so that the reaction between the analyte-specific substance and analyte at these predetermined short reaction times is not in a saturation range or a stationary state. A time which corresponds to approximately half of the long reaction time is typically selected as at least one short reaction time.

The analyte-specific substance is typically provided on any support, typically a test strip or rapid test-strip (also referred to as a reagent carrier or device). Moreover, the analyte or analytes can of course also be determined in liquid tests. However, a determination on test devices (test carriers, above all test strips) is typical on which the analyte-specific substances or reagents used to determine the analyte are located in one or more zones in a dry—and after contact with the sample dissolvable—form where the detectable signal is detected in a detection zone and typically in a separate area of the detection zone. All commercially available test strips which in particular are suitable for quantitatively determining an analyte after a predetermined fixed time value can be used in the method according to the invention.

The limits of the measuring range of the test strip that is used can be extended by a factor of between about 2 and about 5 and typically of more than about 3 by the method according to the invention.

According to another aspect of the present invention, further analytes are qualitatively and/or quantitatively determined on the same support in addition to the analyte that is to be determined quantitatively. Then correspondingly more analyte-specific substances are present on the support. In this case it may in addition be expedient to use detection reagents coupled to analyte-specific substances which enable a quantitative or qualitative determination of all analytes by means of a single test format, for example, an enzymatic test, an electrochemiluminescence test, a fluorescence or absorption test, or a turbidimetric test. Of course different defection reagents for the different analyte-specific substances may be present on a single test strip.

In a typical embodiment the Roche® CARDIAC proBNP test strip is used.

Thus, the measuring range of the Roche CARDIAC® proBNP test strip, which is in a range of between about 60 and about 3000 pg/ml can be extended by the method according to the invention to a range of between about 60 and about 100,00 pg/ml. A typical embodiment of the present invention therefore concerns the quantitative determination of an analyte concentration wherein the analyte is in turn typically selected from troponin T, myoglobin, D-dimer and NT-proBNP. In the case of NT-proBNP the determination is for example carried out in a range of between about 3000 and about 10000 pg/ml with a short reaction time between analyte-specific substance and analyte of between about 3 and about 9 minutes and typically about 8 minutes. The determination of NT-proBNP in a concentration range of between about 60 and about 3000 pg/ml is typically carried out with a long reaction time of between about 10 and about 15 minutes and typically about 12 minutes.

The detectable signal which results from the reaction between analyte and analyte-specific substance is typically quantitatively determined by optical methods and in particular, by reflection photometric or fluorimetric detection or electrochemical luminescence. Other typical quantitative methods of determination include measurements of a change in dielectric constant changes in magnetic fields or a change in the angle of the optical rotation of polarized light.

In a further typical embodiment of the present invention, the method is carried out in an automated form, typically in an automated analyser.

Another aspect of the present invention concerns a device for carrying out the method according to the invention. This device comprises a storage element on which the calibration graphs generated once for an analyte are stored. Examples of storage elements include all common data carriers such as ROM keys, hard drives, CDs, disks, DVDs, USB sticks, etc. The stored calibration graphs can then be provided for the consecutive quantitative determination of a plurality of analyte samples.

The method according to the invention can be used to identify patients with acute coronary syndrome and for improving the early detection of acute coronary events, for example to improve the early detection of acute myocardial infarction.

In order that the invention may be more readily understood, reference is made to the following examples, which are intended to illustrate the invention, but not limit the scope thereof.

EXAMPLE 1

Calibration graphs after 6, 8 and 12 minutes reaction time were generated using a Roche CARDIAC® proBNP-test strip. The respective amounts of proBNP were determined by the Elecsys® proBNP reference method (FIG. 1). The calibration graphs show that the slope decreases as the reaction time decreases. As a consequence the signal amplitude and thus the sensitivity increases at higher concentrations of more than 3000 pg/ml.

Figure 2:
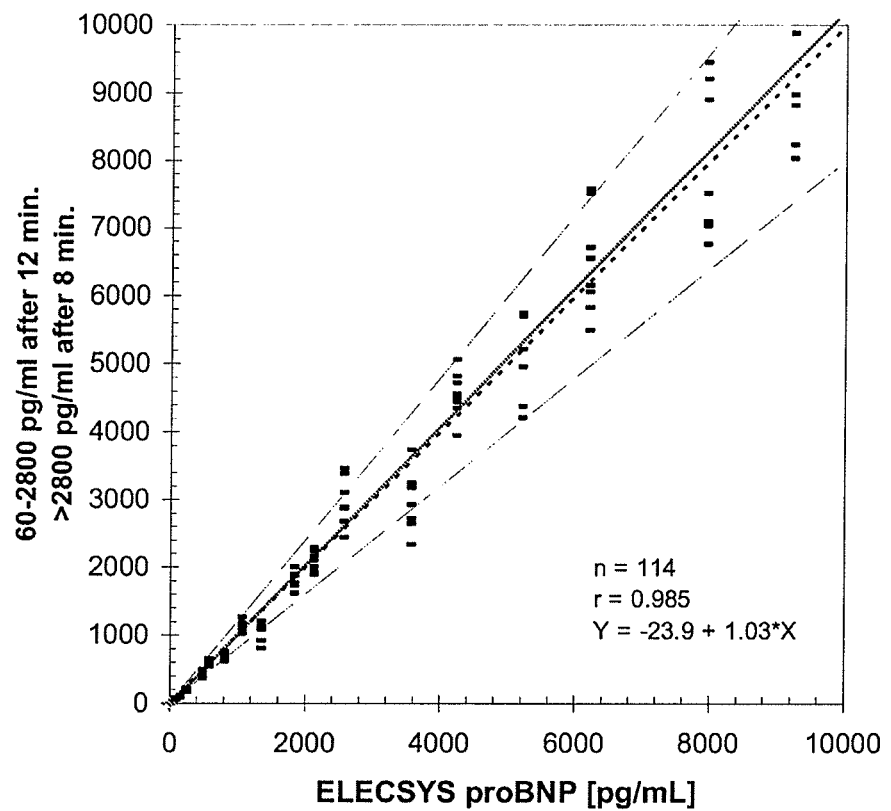
FIG. 2 shows a comparison between the method according to an embodiment of the present invention using a CARDIAC® proBNP test strip and the Elecsys® proBNP test.

A method comparison between the CARDIAC® proBNP test used according to the invention and the Elecsys® proBNP test (FIG. 2) is obtained by evaluating the concentration ranges of 60-2800 pg/ml after 12 minutes and concentrations of more than 2800 pg/ml (which corresponds to an empirically determined or defined reflectance value) after 8 minutes.

A comparison of the measurements with the Elecsys® proBNP reference method showed that the CARDIAC® proBNP test carried out according to the invention with the two different reaction times has a quantitative measuring range of 60 to about 10000 pg/ml. In comparison to the conventional evaluation after 12 minutes which has an upper limit of the measuring range of 3000 pg/ml, the upper limit of the measuring range was thus increased by more than three-fold.

It is noted that terms like "preferably", "commonly", and "typically" are not utilized herein to limit the scope of the claimed invention or to imply that certain features are critical, essential, or even important, to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the preset invention is not necessarily limited to these preferred aspects of the invention.

What is claimed is:

1. A method for the quantitative determination of an analyte in a sample comprising:
    (a) providing a test strip comprising an analyte-specific substance which is able to undergo a reaction which generates a detectable signal when it is contacted with an analyte,
    (b) providing at least two calibration graphs which have been generated by reacting in each case the same analyte-specific substance with different amounts of in each case the same test analyte for in each case a predetermined reaction time,
    (c) contacting the analyte-specific substance with a sample which contains the analyte to be detected,
    (d) measuring a first signal at a first predetermined reaction time for which a first calibration graph according to (b) is provided, wherein the reaction between the analyte to be determined and the analyte specific substance is not in a saturation range or stationary state at the first predetermined reaction time,
    (e) measuring a second signal at a second predetermined reaction time for which a second calibration graph according to (b) is provided, wherein the reaction between the analyte to be determined and the analyte specific substance is in a saturation range or stationary state at the second predetermined reaction time,
    (f) comparing the signals measured according to steps (d) and (e) to an empirical concentration limit to determine which of the signals enables a sufficient accuracy for the quantitative determination of the analyte to be determined, and
    (g) quantitatively determining the analyte to be determined on the basis of the more accurate of the first signal and the second signal.

2. The method according to claim 1, wherein the accuracy of the quantitative determination of the analyte to be determined is checked using the slope of the calibration graphs.

3. The method according to claim 1, wherein the test analyte and the analyte to be determined quantitatively are identical.

4. The method according to claim 1, wherein two or three calibration graphs are determined.

5. The method according to claim 1, wherein the accuracy for the amount of analyte to be determined is achieved by observing the calibration graph that has the greatest slope for the corresponding amount of test analyte out of all predetermined calibration graphs.

6. The method according to claim 1, wherein the limits of the measuring range for the analyte to be determined are extended by a factor of about 2 to about 5.

7. The method according to claim 1, wherein the sample is derived from a body fluid and the limits of the measuring range for the analyte to be determined are extended by a factor greater than about 3.

8. The method according to claim 7, wherein the body fluid is selected from blood, plasma, serum, saliva, urine and combinations thereof.

9. The method according to claim 1 further comprising qualitatively and/or quantitatively determining one or more additional analytes at the same time as the analyte to be determined quantitatively.

10. The method according to claim 1, wherein the analyte is selected from the group consisting of nucleic acids, lipids, carbohydrates, and proteins.

11. The method according to claim 1, wherein the analyte is selected from the group consisting of DNA, RNA, antibodies, antigens, metabolic products, hormones, viruses, microorganisms, cells, cardio-specific markers, neurohormonal markers, ischaemic markers and muscle- specific markers.

12. The method according to claim 1, wherein at least one cardiospecific marker selected from the group consisting of troponin T, myoglobin, D-dimer and NT-proBNP is determined.

13. The method according to claim 1, wherein the analyte-specific substance is selected from the group consisting of antibodies, receptors that can bind to the analyte, antigens, lectin, nucleic acids and nucleic acid analogues.

14. The method according to claim 1, wherein the analyte-specific substance is coupled to a detection reagent.

15. The method according to claim 1, wherein the reaction between analyte and analyte-specific substance is an immunological reaction.

16. The method according to claim 1, wherein the quantitative determination is carried out by optical methods.

17. The method according to claim 16, wherein the optical method is selected from reflection photometric or fluorimetric detection or electrochemiluminescence.

18. The method according to claim 1, wherein the method is conducted with an automated analyzer.

19. A method for the quantitative determination of an analyte in a sample comprising:
(a) providing test strip comprising a solid support having in a dry form an analyte-specific substance in one of a plurality of zones, wherein the analyte specific substance is dissolvable in the sample and comprises a member of a detection system or an enzyme that is able to undergo a reaction which generates a detectable signal;

(b) providing at least two calibration graphs which have been generated by reacting in each case the same analyte-specific substance with different amounts of in each case the same test analyte for in each case a predetermined reaction time,
(c) contacting the sample with the test strip;
(d) measuring a first signal in a detection zone of the test strip at a first predetermined reaction time for which a first calibration graph according to (b) is provided, wherein the reaction between the analyte to be determined and the analyte specific substance is not in a saturation range or stationary state at the first predetermined reaction time;
(e) measuring a second signal in the detection zone at a second predetermined reaction time for which a second calibration graph according to (b) is provided, wherein the reaction between the analyte to be determined and the analyte specific substance is in a saturation range or stationary state at the second predetermined reaction time;
(f) comparing the signals measured according to (d) and (e) to an empirical concentration limit to determine which of the signals enables a sufficient accuracy for the quantitative determination of the analyte to be determined; and
(g) quantitatively determining the analyte to be determined on the basis of the more accurate of the first signal and the second signal.

20. The method of claim 1, wherein the test strip comprises a solid support having in a dry form an analyte-specific substance in one of a plurality of zones, wherein the analyte specific substance is dissolvable in the sample and comprises a member of a detection system or an enzyme that is able to undergo a reaction which generates a detectable signal.

21. The method of claim 1, wherein the first predetermined reaction time is about one-half of the second predetermined reaction time.

22. The method of claim 1, wherein the first predetermined reaction time is about 3-9 minutes and the second predetermined reaction time is about 10-15 minutes.

23. The method of claim 21, wherein the analyte to be determine is N-terminal pro-Brain Natriuretic Peptide (NT-proBNP).

24. The method of claim 1, further comprising measuring a further signal and comparing the further signal to the empirical concentration limit to determine which of the signals enables a sufficient accuracy for the quantitative determination of the analyte to be determined, and quantitatively determining the analyte to be determined on the basis of the more accurate of the first signal the second signal and the further signal.

* * * * *